United States Patent
Feith et al.

(10) Patent No.: US 11,786,717 B2
(45) Date of Patent: Oct. 17, 2023

(54) SELF-FLUSHING CONNECTOR

(71) Applicant: CareFusion 303, Inc., San Diego, CA (US)

(72) Inventors: Raymond P. Feith, Chino Hills, CA (US); Jake Randolph Smith, Durham, NC (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 17/954,195

(22) Filed: Sep. 27, 2022

(65) Prior Publication Data
US 2023/0015576 A1  Jan. 19, 2023

Related U.S. Application Data

(62) Division of application No. 16/393,847, filed on Apr. 24, 2019, now Pat. No. 11,458,293.
(Continued)

(51) Int. Cl.
*A61M 39/22* (2006.01)
*A61M 5/14* (2006.01)
*A61M 39/24* (2006.01)

(52) U.S. Cl.
CPC ............ *A61M 39/225* (2013.01); *A61M 5/14* (2013.01); *A61M 2005/1403* (2013.01);
(Continued)

(58) Field of Classification Search
CPC .. A61M 39/26; A61M 39/223; A61M 39/105; A61M 29/225
See application file for complete search history.

(56) References Cited

U.S. PATENT DOCUMENTS 5,020,562 A  6/1991 Richmond et al.
5,356,375 A * 10/1994 Higley .................. A61M 5/36
604/35
(Continued)

FOREIGN PATENT DOCUMENTS

CN  101062437 A  10/2007
CN  105163796 A  12/2015
(Continued)

OTHER PUBLICATIONS

Chinese Office Action for Application No. 201980028018.3, dated Mar. 18, 2022, 15 pages including translation.
(Continued)

*Primary Examiner* — Courtney B Fredrickson
(74) *Attorney, Agent, or Firm* — Morgan, Lewis & Bockius LLP

(57) ABSTRACT

A self-flushing connector includes a housing having a cavity, a first inlet port, a second inlet port, and an outlet port. A collapsible valve is disposed within the cavity. A first flow path extends from the first inlet port to the outlet port. The first inlet port and the second inlet port are fluidly connected through a gap defined between the body of the collapsible valve and an inner wall of the housing defining the cavity. A second flow path extends from the second inlet port to the first flow path. When the collapsible valve is in a closed state, the collapsible valve fluidly disconnects the second flow path from the first flow path while allowing fluid to flow through the first flow path. When the collapsible valve is in an open state, the second flow path is fluidly connected to the first flow path.

14 Claims, 3 Drawing Sheets

Related U.S. Application Data

(60) Provisional application No. 62/662,098, filed on Apr. 24, 2018.

(52) U.S. Cl.
  CPC .............. *A61M 2039/242* (2013.01); *A61M 2039/2433* (2013.01); *A61M 2039/2493* (2013.01)

(56) References Cited

U.S. PATENT DOCUMENTS

| | | | | |
|---|---|---|---|---|
| 5,439,451 | A | * | 8/1995 | Collinson ............. A61M 39/26 604/247 |
| 8,715,222 | B2 | | 5/2014 | Truitt |
| 9,278,205 | B2 | | 3/2016 | Quach |
| 9,375,561 | B2 | | 6/2016 | Mansour |
| 2006/0027270 | A1 | | 2/2006 | Truitt |
| 2006/0163515 | A1 | * | 7/2006 | Ruschke ............... A61M 39/26 251/149.7 |
| 2016/0325085 | A1 | | 11/2016 | Chelak |
| 2017/0290216 | A1 | * | 10/2017 | Truitt .................. A61M 39/105 |
| 2018/0021502 | A1 | * | 1/2018 | Guala .................. A61M 39/105 137/320 |

FOREIGN PATENT DOCUMENTS

| | | |
|---|---|---|
| EP | 0430398 A2 | 6/1991 |
| EP | 2777755 | 9/2014 |
| JP | H03173575 A | 7/1991 |
| JP | 2016515853 A | 6/2016 |
| WO | WO2013146740 A1 | 10/2013 |
| WO | WO-2014143528 A1 | 9/2014 |
| WO | WO2014164881 A1 | 10/2014 |
| WO | WO2015100135 A2 | 7/2015 |
| WO | WO2017074693 A1 | 5/2017 |

OTHER PUBLICATIONS

International Preliminary Report on Patentability from the International Preliminary Examining Authority for Application No. PCT/US2019/028993, dated Aug. 6, 2020, 10 pages.

International Preliminary Report on Patentability from the International Preliminary Examining Authority for Application No. PCT/US2019/028993, dated Nov. 18, 2020, 19 pages.

International Search Report and Written Opinion for Application No. PCT/US2019/028993, dated Aug. 8, 2019, 15 pages.

Written Opinion from the International Preliminary Examining Authority for Application No. PCT/US2019/028993, dated Apr. 8, 2020, 9 pages.

Japanese Office Action for Application No. 2020-559372, dated Feb. 8, 2023, 4 pages including translation.

European Office Action for Application No. 19729900.1, dated Jul. 7, 2023, 8 pages.

\* cited by examiner

SELF-FLUSHING CONNECTOR

CROSS-REFERENCE TO RELATED APPLICATIONS

This application is a divisional of U.S. patent application Ser. No. 16/393,847, filed on Apr. 24, 2019, which claims priority to U.S. Provisional Application No. 62/662,098, filed on Apr. 24, 2018, in the United States Patent and Trademark Office, the disclosure of each of which is incorporated herein by reference in its entirety

TECHNICAL FIELD

The present disclosure generally relates to the administration of medication by infusion and, more particularly, to a self-flushing connector.

BACKGROUND

An intravenous (IV) bag, bottle, syringe, or other container that contains infusion medication or solution is hung from a rack to administer the infusion solution. A tube is connected between the container and an infusion pumping system. A catheter at the end of the tube is inserted into a patient for an IV infusion. The tube may be part of an assembly that includes fittings, connectors, valves, and pumping elements and is frequently referred to as an "IV set." The infusion solution is administered to the patient when the infusion pumping system is started.

Existing IV connectors include Y-site connectors that allow additional medication dispensed via the side flow channel to be administered to the patient along with the medication or fluid flowing through the main flow channel. After dispensing the additional medication, a caregiver flushes additional medication and fluid through the side flow channel to ensure that all of the additional medication dispended via the Y-site connector is pushed into the main flow channel so that no additional medication is left in the side flow channel.

SUMMARY

Patients (e.g., infants) may be sensitive to additional fluid administered on top of the already-administered medications. In such a case, the flush of additional medication and fluid administered through the side flow channel may be required since the additional medication may be a low volume that may not flush into the main flow channel by itself, or may be caught in a "dead space" area (i.e., the side channel flow). These would not be suitable for those patients who may be sensitive to additional fluid.

Providing a connector that minimizes the "dead space" area, and therefore the additional fluid that may be needed to push the medication—that is dispensed via the side flow channel—and that gets stuck in the "dead space" into the main flow channel would be advantageous. Providing an infusion pump that accomplishes this while also being more reliable, less expensive, and/or quieter than current infusion pumps would be an additional advantage. Described herein are connectors that achieve these desired functions and objectives.

In accordance with various embodiments of the present disclosure, a self-flushing connector includes a housing having a cavity, a first inlet port, a second inlet port, and an outlet port. The first inlet port extends from a sidewall of the housing to the cavity, the second inlet port extends from an upper portion of the housing to the cavity, and the outlet port is fluidly connected with the first inlet port and the cavity. A collapsible valve is disposed within the cavity. A first flow path extends from the first inlet port to the outlet port. The first inlet port and the second inlet port are fluidly connected through a gap defined between the body of the collapsible valve and an inner wall of the housing defining the cavity. A second flow path extends from the second inlet port to the first flow path. When the collapsible valve is in a closed state, the collapsible valve fluidly disconnects the second flow path from the first flow path while allowing fluid to flow through the first flow path. When the collapsible valve is in an open state, the second flow path is fluidly connected to the first flow path to allow fluid entering the second flow path to be flushed out through the outlet port.

In some embodiments, a self-flushing connector assembly includes a housing having a cavity, a first inlet port, a second inlet port, and an outlet port. A collapsible valve is disposed within the cavity of the housing. The collapsible valve includes a head, a body extending from the head, and a shoulder defined on a portion of the body. A first flow path extends from the first inlet port into the cavity of the housing and around the body of the collapsible valve to the outlet port. A second flow path extends from the second inlet port into the cavity of the housing and around the head of the collapsible valve to the first flow path. When the collapsible valve is in a closed state, the head of the collapsible valve fluidly disconnects the second flow path from the first flow path. When the collapsible valve is in an open state, the second flow path is fluidly connected to the first flow path.

In some embodiments, a self-flushing connector includes a housing having a cavity extending longitudinally therein, and a collapsible valve disposed within the cavity of the housing. The collapsible valve includes a head, and a body extending from the head. The self-flushing connector further includes a first inlet port extending from a sidewall of the housing, and a second inlet port extending from an opposite sidewall of the housing. The first and second inlet ports define a flow path therebetween, and a second inlet port extends from an upper portion of the housing into the cavity of the housing. When the collapsible valve is in a closed state, the head of the collapsible valve obstructs fluid flow from the second inlet port into the flow path. When the collapsible valve is in an open state, the second inlet port is fluidly connected to the flow path.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The disclosed embodiments of a connector provide a reliable method of delivering a fluid preventing additional fluid to push additional medication dispensed via a side flow channel into the main flow channel.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

The methods and systems disclosed herein are presented in terms of an infusion pump for the delivery of medical fluid to a patient. It will be apparent to those of ordinary skill in the art that the disclosed concepts may be applied to a variety of mechanisms utilizing connectors.

Aspects of the subject technology relate to a connector that that minimizes additional fluid to push the medication dispensed via the side flow channel into the main flow channel. This mechanism eliminates the need for additional flushing fluid when there is sensitivity to fluid volume entering patients. This mechanism may reduce cost of the IV set since the Y-connector is not required and tubing connection between the Y-connector and valve is also not required.

Figure 1:
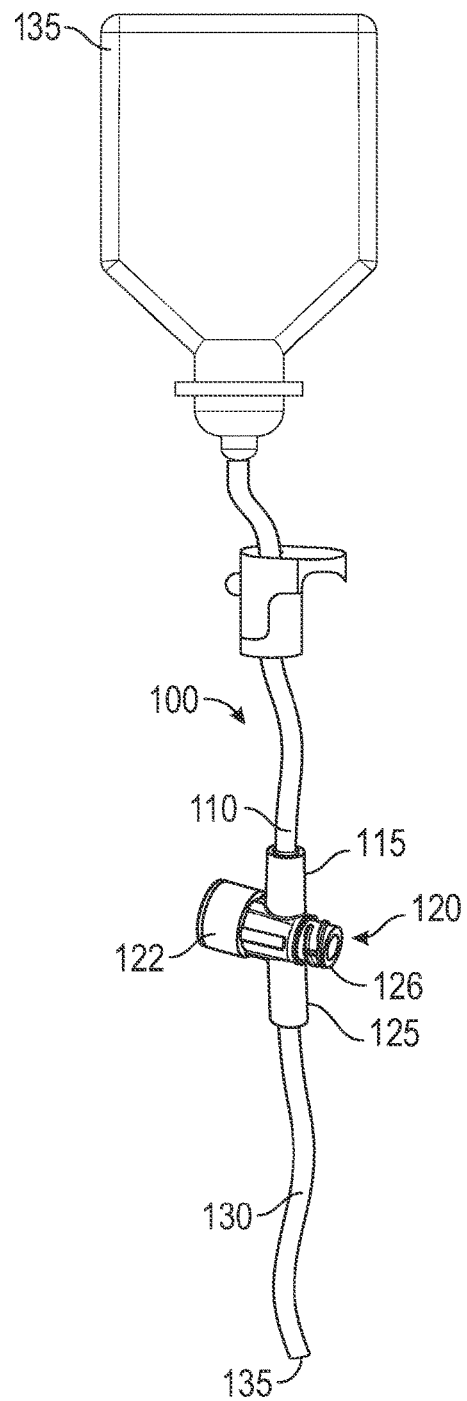
FIG. 1 depicts a connector assembly including a self-flushing connector, according to certain aspects of the disclosure.

FIG. 1 illustrates a connector assembly 100 that includes an inlet tube 110, a connector 120, and an outlet tube 130 according to certain aspects of the disclosure. The inlet tube 110 may be connected to a first inlet port 115 of the connector 120, and the outlet tube 130 may be connected to an outlet port 125 of the connector 120. The connector 220 may further include a second inlet port 226 extending from an upper end portion of the housing 122. The second inlet port 126 may be configured to connect to a syringe (not shown), and allow additional fluid that is different from the fluid from an IV bag 135, that includes an infusion medication or solution which may contain drugs or other fluid to be supplied to the patient for treatment, to be dispensed into the connector 120. In operation, medication for delivery to a patient flows from the IV bag 135 through the inlet tube 110 and into the inlet port 115 of the connector 120. The medication then flows from the inlet port 115, into the outlet port 125 of the connector 120, and through the outlet tube 130 to the patient via a catheter (not shown) attached at the outlet 135 of the outlet tube 130.

Various embodiments of the present disclosure relate to a self-flushing connector that overcomes the deficiencies of traditional Y-site connectors. For example, various embodiments of the present disclosure are directed to a self-flushing IV connector that eliminates the need for having to flush additional medication and fluid through a side-flow channel in order to ensure that all medication is dispensed and not caught in a "dead space" of the side-flow channel, as customarily experienced with conventional connector assemblies utilizing Y-site connectors to connect the separate side-flow channel to the main flow channel. Accordingly, the self-flushing connector of the various embodiments described herein minimizes or completely eliminates the need for dispensing additional fluid to push the low volume medication dispensed via the side flow channel into the main flow channel to reach the patient.

Figure 2:
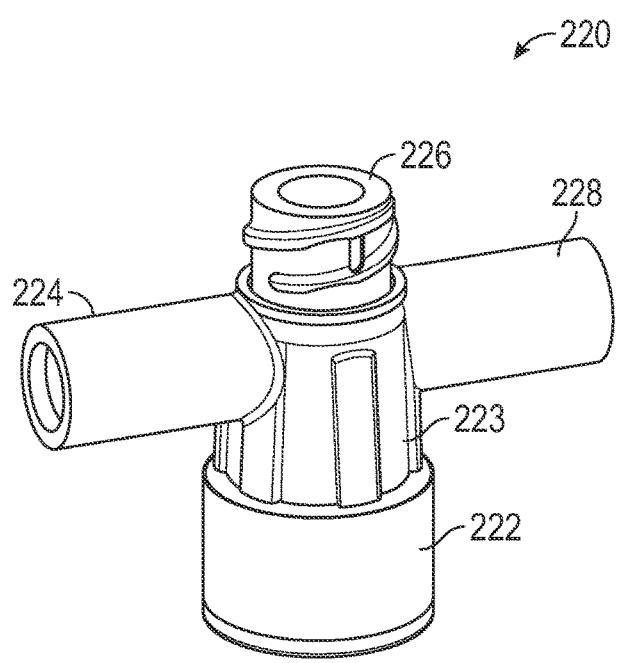
FIG. 2 depicts an isometric view of a self-flushing connector, according to certain aspects of the disclosure.

FIG. 2 illustrates an isometric view of a self-flushing connector, according to certain aspects of the disclosure. In accordance with various embodiments of the present disclosure, the connector 220 is similar or corresponds in structure to the connector 120 illustrated in FIG. 1. As depicted, the connector 220 includes a housing 222, a first inlet port 224 extending from a sidewall 223 of the housing 222, and a second inlet port 226 extending from an upper end portion of the housing 222. The self-flushing connector 220 further includes an outlet port 228 aligned with the first inlet port 224. In some embodiments, the first inlet port 224 and the outlet port 228 are fluidly connected to define a main flow channel. As depicted in FIG. 2 with further reference to FIG. 1, the first inlet port 224 may be fluidly connected to an inlet tube (i.e., the inlet tube 110 of FIG. 1), and allow the fluid from the IV 135 bag to flow into the connector 220 from the inlet tube 110. In accordance with some embodiments, the second inlet port 226 is configured to connect to a syringe (illustrated in the embodiments of FIG. 4), and allows additional fluid that is different from the fluid from the IV bag 135 to be dispensed into the connector 220. For example, the second inlet port 226 is configured to receive the syringe which remains attached to the inlet port 226 of the connector 200, for example for 10 to 30 seconds to allow the fluid from the main flow channel to flush the additional fluid added from the syringe. As depicted in FIGS. 1 and 2, the outlet port 228 may be connected to the outlet tube 130 to allow the fluid from the IV bag 135 and the additional fluid from the syringe to exit the connector 220.

Figure 3:
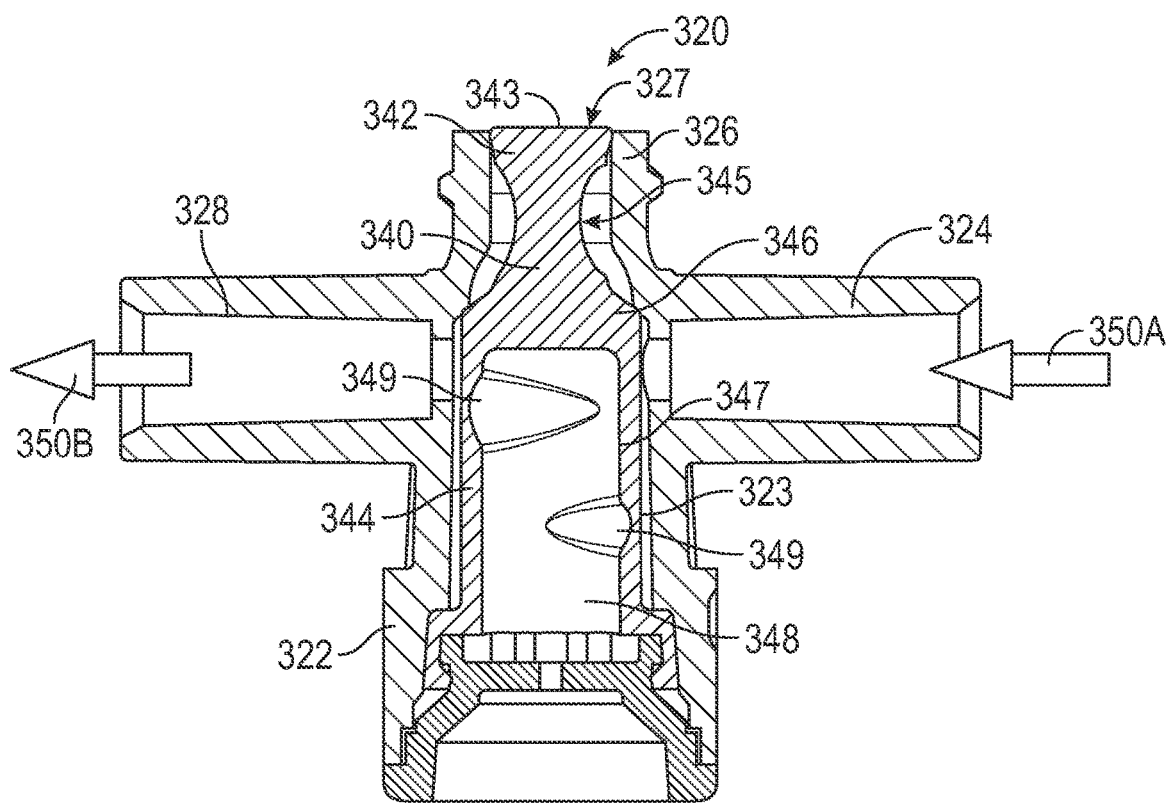
FIG. 3 depicts a cross-sectional view of a self-flushing connector, according to certain aspects of the disclosure.

FIG. 3 illustrates a cross-sectional view of a self-flushing connector 320. In accordance with various embodiments of the present disclosure, the connector 320 is similar or corresponds in structure to the connector 220 illustrated in FIGS. 1 and 2. In particular, the connector 320 of FIG. 3 represents a cross-sectional view of the connector 220. Similar to the connector 220, the connector 320 includes a housing 322, a first inlet port 324 extending from a sidewall of the housing 322, and, and a second inlet port 326 extending from an upper end portion of the housing 322. The self-flushing connector 320 further includes an outlet port 328. The housing 322 may include a cavity 323 extending longitudinally within the housing 322. The cavity 323 may be fluidly connected with the first inlet port 324, the second inlet port 326, and the outlet port 328.

In accordance with some embodiments, the connector 320 may further include a collapsible valve 340 disposed within the cavity 323 of the housing 322. As depicted, the collapsible valve 340 may include a head 342 defined at an upper portion of the collapsible valve 340, and a body 344 extending longitudinally from the head 342. A diameter of a top surface 343 of the head 342 may be larger than a diameter of an opening 327 of the second inlet port 326 sealing the opening 327 of the second inlet port 326. In some embodiments, the connector 320 may further include a neck portion 345 positioned below the head 342, the neck portion of 345 defining a narrowing portion between the head 342 and the body 344, As further illustrated, a shoulder 346 may be defined at a base of the neck portion 345 of the collapsible valve 340. The shoulder 346 may define a widened portion of the body 344 as compared with the head 342 and the neck portion 345. In some embodiments, the body 344 may have a cavity 348 defined therein. In some aspects, an inner wall 347 of the body 344 defining the cavity 348 of the valve 340 may include one or more dimples 349 that allow the valve 340 to deform when pressure is exerted on the valve 340.

FIG. 3 depicts the valve 340 in a closed state. When the valve 340 is in the closed state, the head 342 of the valve 340 may extend into the second inlet port 326. Further, in the embodiments where the diameter of the top surface 343 of the head 342 is larger the diameter of the opening 327 of the second inlet port 326, the head 342 may provide a primary seal to seal the opening 327 of the second inlet port 236 to restrict any fluid from flowing in through the second inlet port 326 when the valve 340 is in a closed state. In some aspects, the area defined by the cavity 323 of the housing 322 may taper or otherwise reduce in size towards the opening 327 of the second inlet port 326. When the valve 340 is in the closed state depicted in FIG. 3, the shoulder 346 of the valve 340 may contact the wall defining the cavity 323 in the narrowed area of the cavity 323, thereby providing a secondary seal for restricting fluid from flowing through the second inlet port 326 and into the cavity 323.

However, even when the valve 340 is in a closed state, fluid may be able to flow from the first inlet port 324 through a gap 525 (illustrated in FIG. 5) between the outer surface of the body 344 of the valve 340 and the inner wall defining the cavity 323 of the housing 322 to the outlet port 328. For example, fluid from the IV bag 135 may flow into the cavity 323 of the housing 322 from the first inlet port 324 in the flow direction illustrated by arrow 350A. The fluid from the IV bag 135 entering the cavity 323 from the first inlet port 324 may then flow around the exterior of the body 344 of the valve 340 through the gap 525 (illustrated in FIG. 5) between the body 344 of the valve 340 and the cavity 323 of the housing 322. The fluid from the IV bag 135 that has flowed into the cavity 323 through the gap 525 (illustrated in FIG. 5) may then exit the cavity 323 through the outlet port 328 as illustrated by arrow 350B. The fluid path created from the first inlet port 324 through the gap 525 (illustrated in FIG. 5) to the outlet port 328 is the main fluid channel of the connector 320.

Figure 4:
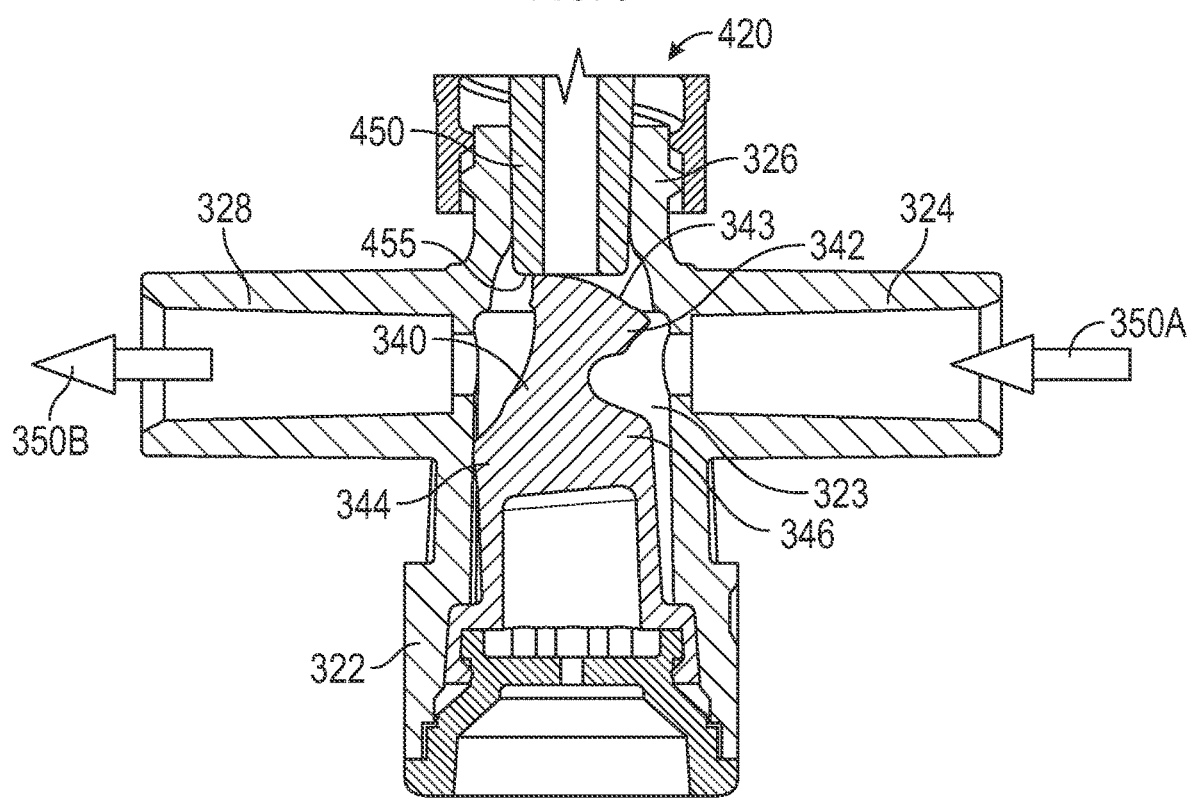
FIG. 4 depicts a cross-sectional view of a self-flushing connector having a syringe inserted therein, according to certain aspects of the disclosure.

FIG. 4 illustrates a cross-sectional view of a self-flushing connector 420 having a syringe inserted therein. In accordance with various embodiments of the present disclosure, the connector 420 is similar or corresponds in structure to the connector 320 illustrated in FIG. 3. In particular, the connector 420 of FIG. 4 represents a cross-sectional view of the connector 320 with a syringe inserted into the second inlet port 326. The connector 420 includes the same parts as those described with respect to the self-flushing connector 320 of FIG. 3, thus a detailed description thereof is omitted.

FIG. 4 depicts the valve 340 in an open state. In accordance with various embodiments of the present disclosure, a syringe 450 may be inserted into or otherwise attached to the second inlet port 326. When the syringe 450 is advanced into the second inlet port 326, a tip 455 of the syringe 450 pushes the head 342 of the valve 340 in the direction of movement of the syringe 450, causing pressure to be exerted on the head 342 of the valve 340. When the pressure is exerted on the head 342, the valve 340 compresses and becomes deformed, thereby moving from the closed state illustrated in FIG. 3 to the open state illustrated in FIG. 4, and allowing fluid to flow into the cavity 323 of the housing 322 through the second inlet port 326. For example, when the valve 340 is deformed as a result of pressure exerted by the syringe 450, and thereby placed in the open state, the fluid path of the second inlet port 326, which was blocked or otherwise occluded by the head 342 of the valve 340 when the valve 340 was in a closed state, is connected to the main flow channel while a continuous flow of the fluid from the IV bag 135 (illustrated in FIG. 1) through the main flow channel (i.e., between the first inlet and the outlet port) is simultaneously maintained. When the syringe 450 is inserted into the second inlet port 326 and attached to the connector 420 to access the valve 340 in order to dispense the additional fluid, the syringe 450 remains attached to the connector 420, for example, for 10 to 30 seconds to allow the fluid from the main flow channel to flush the additional fluid added from the syringe 450.

Figure 5:
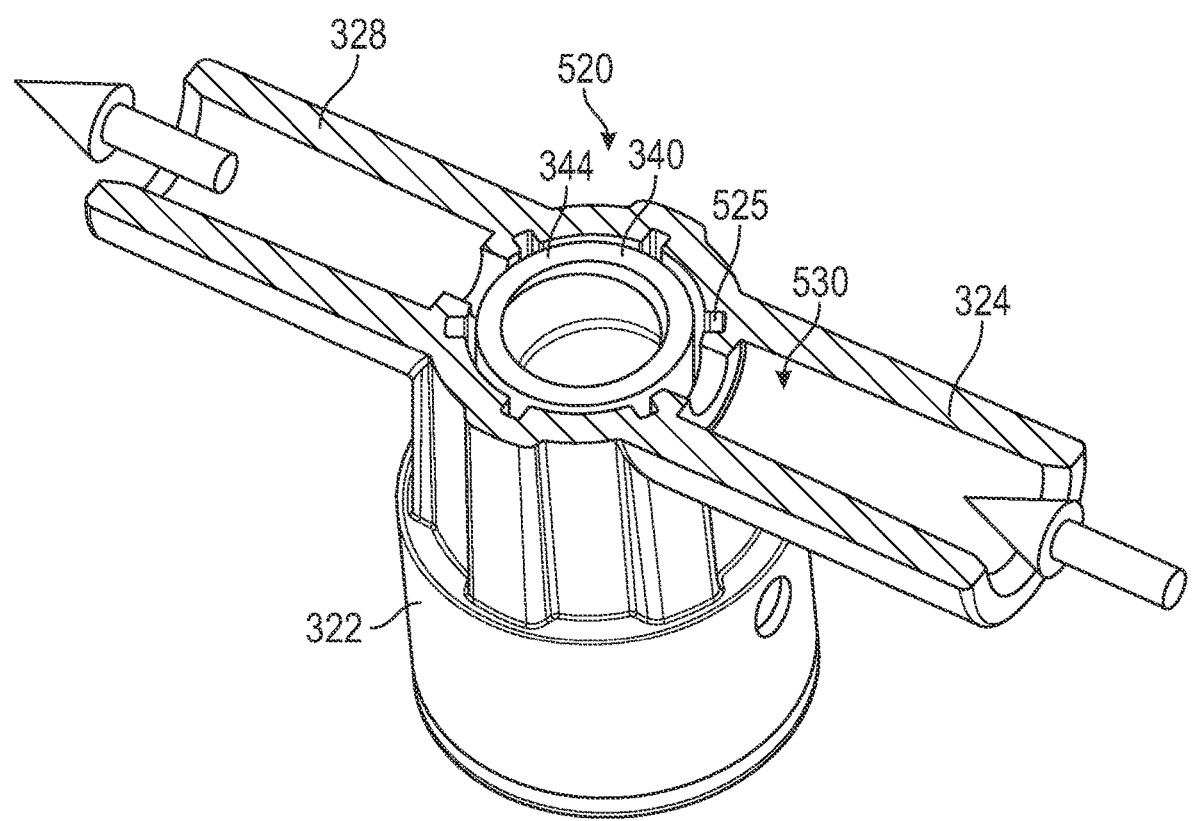
FIG. 5 depicts a cross-sectional view of illustrating a main flow channel of the self-flushing connector according to certain aspects of the disclosure.

FIG. 5 illustrates a cross-sectional view of a connector 520. In accordance with various embodiments of the present disclosure, the connector 520 is similar or corresponds in structure to the connector 320 illustrated in FIG. 3. In particular, the connector 520 of FIG. 5 represents a cross-sectional view of the main flow channel 530 of the connector. The connector 520 includes the same parts as those described with respect FIG. 3, thus a detailed description of the parts is omitted.

FIG. 5 depicts the valve 340 in a closed state. In accordance with various embodiments of the present disclosure, the main flow channel 530 extends from the first inlet port 324 around the body 344 of the valve 340 through the gap 525 which extends between the body 344 of the valve 340 and the inner surface of the housing 322 to the outlet port 328. The aforementioned configuration where a continuously open flow path exists between the first inlet port 324 and the outlet port 328 allows for continuous fluid flow through the main flow channel 530 even when the valve 340 is in the closed state where fluid is restricted from flowing through the second inlet port 326 (illustrated in FIGS. 3 and 4). Since the flow path of the main flow channel 530 is continuously open, when the valve 340 is in the open state, the fluid still flows through the main flow channel 530. In the open state, the additional fluid introduced by syringe 450 into the second inlet 326 port joins the main flow channel 530 and is output (i.e., flushed) from the outlet port 328 along with the fluid flowing into the cavity 323 of the housing 322 from the first inlet port 324.

The self-flushing connector of the various embodiments described herein is advantageous over prior art in that it eliminates the need for multiple syringe pushes to be administered after dispensing a low volume of medication in order to move the low volume of medication from the "dead space" and make sure that the medication reaches the patient. In particular, the connector of the various embodiments described herein is termed a self-flushing connector because a continuously open fluid path exists in the main flow channel between the first inlet port and the outlet port of the connector regardless of whether the collapsible valve is in the open or closed state. Thus, when a syringe is inserted into the second inlet port to dispense additional medication, the fluid flowing through the main flow channel "self-flushes" the additional fluid introduced by syringe into the main flow channel and out of the outlet port to reach the patient. Accordingly, the self-flushing connector of the various embodiments described herein eliminates the need for a clinician or other medical staff to make multiple syringe pushes to flush the additional low volume medication which gets caught in the dead space with connector assemblies employing the traditional Y-site connectors.

Accordingly, the self-flushing IV connector of the various embodiments described herein eliminates the need for having to flush additional medication and fluid through a separate side-flow channel (susceptible to a "dead space") in order to ensure that all medication is dispensed and not caught in the "dead space" of the side-flow channel, as customarily experienced with conventional Y-site connectors. Accordingly, the self-flushing connector of the various embodiments described herein minimizes or completely eliminates the need for additional fluid to push the medication dispensed via the side flow channel into the main flow channel for dispensing to the patient.

A further advantage is realized in that the self-flushing connector of the various embodiments described herein directly connects to a main flow channel of fluid flowing from an IV bag to a patient, thereby eliminating the need for a separate Y-site connector and corresponding tubing for connecting the connector (e.g., a needle-free connector) to the main flow channel between the IV bag and the patient. Accordingly, cost of the connector assembly is advantageously reduced by eliminating the need for the Y-site connector and the corresponding tubing.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: A self-flushing connector, comprising: a housing comprising a cavity, a first inlet port, a second inlet port, and an outlet port, the first inlet port extending from a sidewall of the housing to the cavity, the second inlet port extending from an upper portion of the housing to the cavity, and the outlet port fluidly connected with the first inlet port and the cavity; a collapsible valve disposed within the cavity; a first flow path extending from the first inlet port to the outlet port, the first inlet port and the second inlet port being fluidly connected through a gap defined between the body of the collapsible valve and an inner wall of the housing defining the cavity; and a second flow path extending from the second inlet port to the first flow path, wherein when the collapsible valve is in a closed state, the collapsible valve fluidly disconnects the second flow path from the first flow path while allowing fluid to flow through the first flow path, and wherein when the collapsible valve is in an open state, the second flow path is fluidly connected to the first flow path to allow fluid entering the second flow path to be flushed out through the outlet port.

Clause 2: The self-flushing connector of Clause 1, wherein the collapsible valve comprises a head and a body extending longitudinally from the head, and in the closed state the head extends into the second inlet port to fluidly disconnect the second flow path from the first flow path.

Clause 3: The self-flushing connector of Clause 1, wherein the first inlet port is axially aligned with the outlet port.

Clause 4: The self-flushing connector of Clause 1, wherein the second inlet port is disposed perpendicular to the first inlet port.

Clause 5: The self-flushing connector of Clause 4, wherein the second inlet port is disposed perpendicular to the outlet port.

Clause 6: The self-flushing connector of Clause 1, wherein a body of the collapsible valve comprises a cavity extending therein, and an inner wall of the body defining the cavity includes at least one dimple that allows the valve to deform when pressure is exerted on the valve.

Clause 7: The self-flushing connector of Clause 1, wherein the first inlet port allows a first fluid to flow into the connector, and when the collapsible valve is in the open state, the second inlet port allows a second fluid, different than the first fluid, to flow simultaneously into the connector.

Clause 8: A self-flushing connector assembly, comprising: a housing comprising a cavity, a first inlet port, a second inlet port, and an outlet port; a collapsible valve disposed within the cavity of the housing, the collapsible valve comprising a head, a body extending from the head, and a shoulder defined on a portion of the body; a first flow path extending from the first inlet port into the cavity of the housing and around the body of the collapsible valve to the outlet port; and a second flow path extending from the second inlet port into the cavity of the housing and around the head of the collapsible valve to the first flow path, wherein when the collapsible valve is in a closed state, the head of the collapsible valve fluidly disconnects the second flow path from the first flow path, and wherein when the collapsible valve is in an open state, the second flow path is fluidly connected to the first flow path.

Clause 9: The self-flushing connector of Clause 8, wherein in the closed state, the head of the valve extends into the second inlet port.

Clause 10: The self-flushing connector of Clause 8, wherein the first inlet port is disposed opposite the outlet port.

Clause 11: The self-flushing connector of Clause 8, wherein the second inlet port is disposed perpendicular to the first inlet port.

Clause 12: The self-flushing connector of Clause 11, wherein the second inlet port is disposed perpendicular to the outlet port.

Clause 13: The self-flushing connector of Clause 8, wherein the body of the collapsible valve comprises a cavity extending therein, and an inner wall of the body defining the cavity includes at least one dimple that allows the valve to deform when pressure is exerted on the valve.

Clause 14: The self-flushing connector of Clause 8, wherein the first inlet port allows a first fluid to flow into the connector, and when the valve is in the open state, the second inlet port allows a second fluid, different than the first fluid, to flow simultaneously into the connector.

Clause 15: A self-flushing connector, comprising: a housing comprising a cavity extending longitudinally therein, a collapsible valve disposed within the cavity of the housing, the collapsible valve comprising a head, and a body extending from the head; a first inlet port extending from a sidewall of the housing, and a second inlet port extending from an opposite sidewall of the housing, the first and second inlet ports defining a flow path therebetween; and a second inlet port extending from an upper portion of the housing into the cavity of the housing, wherein when the collapsible valve is in a closed state, the head of the collapsible valve obstructs fluid flow from the second inlet port into the flow path, and wherein when the collapsible valve is in an open state, the second inlet port is fluidly connected to the flow path.

Clause 16: The self-flushing connector of Clause 15, wherein: the flow path comprises a first flow path extending from the first inlet port into the cavity of the housing and around the body of the collapsible valve to the outlet port; and a second flow path extends from the second inlet port, into the cavity of the housing and around the head of the collapsible valve to the first flow path.

Clause 17: The self-flushing connector of Clause 16, wherein the first inlet port allows a first fluid to flow into the connector, and in the open state of the valve, the second inlet port allows a second fluid to flow into the connector, wherein the first fluid and the second fluid are different.

Clause 18: The self-flushing connector of Clause 15, wherein the head of the valve extends into the second inlet port.

Clause 19: The self-flushing connector of Clause 15, wherein the second inlet port is disposed perpendicular to the first inlet port.

Clause 20: The self-flushing connector of Clause 15, wherein the second inlet port is disposed perpendicular to the outlet port.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A self-flushing connector, comprising:
   a housing comprising a sidewall having an inner surface forming a housing cavity, a first inlet port extending through the sidewall, a second inlet port aligned longitudinally with the housing cavity, and an outlet port extending through the sidewall, wherein a plurality of longitudinal grooves extend along the inner surface of the sidewall, and the first inlet port and the outlet port intersect the housing cavity along the plurality of longitudinal grooves; and
   a collapsible valve comprising a head and a body, and positioned longitudinally within the housing cavity to form a main flow channel extending between the first inlet port, the outlet port, an outer surface of the body, and the inner surface of the sidewall, wherein the plurality of longitudinal grooves form a gap between the outer surface of the body and the inner surface of the sidewall;
   wherein, when the valve is in a closed state, the head of the collapsible valve resists a fluid flow from the second inlet port to the main flow channel, and when the valve is in an open state, the second inlet port is fluidly connected to the main flow channel such that the first inlet port, the second inlet port, and the outlet port are fluidly coupled.

2. The self-flushing connector of claim 1, wherein the first inlet port is axially aligned with the outlet port.

3. The self-flushing connector of claim 1, wherein the second inlet port is disposed perpendicular to the first inlet port.

4. The self-flushing connector of claim 1, wherein the second inlet port is disposed perpendicular to the outlet port.

5. The self-flushing connector of claim 1, wherein the body of the collapsible valve comprises an inner wall forming a valve cavity.

6. The self-flushing connector of claim 5, wherein the inner wall of the body includes at least one dimple that allows the collapsible valve to deform when a longitudinal force is exerted on the head of the valve.

7. The self-flushing connector of claim 1, wherein the first inlet port allows a first fluid to flow into the connector, and when the collapsible valve is in the open state, the second inlet port allows a second fluid, different than the first fluid, to flow simultaneously into the connector.

8. A self-flushing connector, comprising:
a housing comprising a first inlet port, a second inlet port, an outlet port, an inner surface forming a housing cavity fluidly coupled with the first and second inlet ports and the outlet port, and a plurality of longitudinal grooves extending along the inner surface of the housing such that the first inlet port and the outlet port intersect the housing cavity along the plurality of longitudinal grooves; and
a collapsible valve comprising a head and a body that extends longitudinally from the head, the collapsible valve positioned within the housing cavity such that the plurality of longitudinal grooves form a gap between an outer surface of the body and the inner surface of the housing, and a continuously open flow path extends between the first inlet port and the outlet port, wherein, in a closed state, the head of the collapsible valve extends into the second inlet port to obstruct a fluid pathway from the second inlet port to the continuously open flow path, and in an open state, the fluid pathway is fluidly coupled with the continuously open flow path.

9. The self-flushing connector of claim 8, wherein the first inlet port is axially aligned with the outlet port.

10. The self-flushing connector of claim 8, wherein the second inlet port is disposed perpendicular to the first inlet port.

11. The self-flushing connector of claim 8, wherein the second inlet port is disposed perpendicular to the outlet port.

12. The self-flushing connector of claim 8, wherein the body of the collapsible valve comprises an inner wall forming a valve cavity.

13. The self-flushing connector of claim 12, wherein the inner wall of the body includes at least one dimple that allows the collapsible valve to deform when a longitudinal force is exerted on the head of the valve.

14. The self-flushing connector of claim 8, wherein the first inlet port allows a first fluid to flow into the connector, and when the collapsible valve is in the open state, the second inlet port allows a second fluid, different than the first fluid, to flow simultaneously into the connector.

* * * * *